US008500751B2

(12) United States Patent
Rudakov et al.

(10) Patent No.: US 8,500,751 B2
(45) Date of Patent: Aug. 6, 2013

(54) MEDICAL DEVICE

(75) Inventors: Leon Rudakov, Belmont, CA (US);
Michael O'Connor, Singapore (SG);
Deepak Gandhi, Singapore (SG)

(73) Assignee: Merlin MD Pte Ltd, Singapore (SG)

( * ) Notice: Subject to any disclaimer, the term of this patent is extended or adjusted under 35 U.S.C. 154(b) by 276 days.

(21) Appl. No.: 11/586,899

(22) Filed: Oct. 25, 2006

(65) Prior Publication Data

US 2007/0100426 A1     May 3, 2007

Related U.S. Application Data

(63) Continuation-in-part of application No. 10/580,139, filed as application No. PCT/SG2004/000407 on Dec. 13, 2004.

(30) Foreign Application Priority Data

Mar. 31, 2004 (SG) .............................. 200401735-6

(51) Int. Cl.
*A61F 2/06* (2006.01)
*A61F 11/00* (2006.01)

(52) U.S. Cl.
USPC .......................... 606/108; 623/1.39; 623/1.13

(58) Field of Classification Search
CPC ........................................................ A61F 2/06
USPC ............. 623/1.13, 1.15, 1.38–1.46; 606/108
IPC ........................................................ A61F 2/06
See application file for complete search history.

(56) References Cited

U.S. PATENT DOCUMENTS 4,100,309 A    7/1978   Micklus et al.
4,503,569 A    3/1985   Dotter (Continued)

FOREIGN PATENT DOCUMENTS

EP        0754435      1/1997
EP        0 815 806     1/1998

(Continued)

OTHER PUBLICATIONS

Chatterjee, S., Lactosylceramide Stimulates Aortic Smooth Muscle Cell Proliferation, Biochemical and Biophysical Research Communications, Dec. 16, 1991, pp. 554-561, vol. 181, No. 2., Academic Press, Orlando FL.

(Continued)

*Primary Examiner* — Jason-Dennis Stewart
(74) *Attorney, Agent, or Firm* — James W. Hill; Nathan S. Smith; McDermott Will & Emery LLP

(57) ABSTRACT

A method for treating a bifurcation or trifurcation aneurysm (201) occurring on a first artery, the first artery and a second artery joining to a third artery, the method comprising: inserting a medical device (202) such that it is at least partially located in the first artery and is at least partially located in the third artery; expanding the medical device (202) from a first position to a second position, said medical device (202) is expanded radially outwardly to the second position such that the exterior surface of said medical device (202) engages with the inner surface of the first and third arteries so as to maintain a fluid pathway through said arteries; and positioning the medical device (202) such that a membrane (203) of the medical device (202) is located against an aneurysm neck of the aneurysm (201) to obstruct blood circulation to the aneurysm (201) when the medical device (202) is expanded to the second position, and at least a portion of the membrane (203) is secured to the medical device (202) to maintain the position of the membrane (203) relative to the medical device (202) when expanded to the second position; wherein the membrane (203) is permeable and porous, the size of the pores of the membrane (203) and the ratio of the material surface area of the membrane (203) being such that blood supply to perforators and/or microscopic branches of main brain arteries is permitted to improve healing of the first artery but blood supply to the aneurysm (201) is prevented.

60 Claims, 13 Drawing Sheets

U.S. PATENT DOCUMENTS

| | | | |
|---|---|---|---|
| 5,026,607 A | 6/1991 | Kiezulas | |
| 5,041,441 A | 8/1991 | Radin et al. | |
| 5,234,457 A | 8/1993 | Anderson | |
| 5,356,423 A | 10/1994 | Tihon et al. | |
| 5,405,377 A | 4/1995 | Cragg | |
| D359,802 S | 6/1995 | Fontaine | |
| 5,421,955 A | 6/1995 | Lau et al. | |
| 5,443,458 A | 8/1995 | Eury | |
| 5,514,154 A | 5/1996 | Lau et al. | |
| 5,562,725 A | 10/1996 | Schmitt et al. | |
| 5,589,563 A | 12/1996 | Ward et al. | |
| 5,601,593 A | 2/1997 | Freitag | |
| 5,620,763 A | 4/1997 | House et al. | |
| 5,630,840 A | 5/1997 | Mayer | |
| 5,632,840 A | 5/1997 | Campbell | |
| 5,637,113 A | 6/1997 | Tartaglia et al. | |
| 5,639,278 A | 6/1997 | Dereume et al. | |
| 5,658,331 A | 8/1997 | Della Valle et al. | |
| 5,700,285 A | 12/1997 | Myers et al. | |
| D390,957 S | 2/1998 | Fontaine | |
| 5,718,973 A | 2/1998 | Lewis et al. | |
| 5,735,893 A | 4/1998 | Lau et al. | |
| 5,744,515 A | 4/1998 | Clapper | |
| 5,766,238 A | 6/1998 | Lau et al. | |
| 5,769,884 A * | 6/1998 | Solovay | 623/1.13 |
| 5,810,870 A | 9/1998 | Myers et al. | |
| 5,843,172 A | 12/1998 | Yan | |
| 5,858,556 A | 1/1999 | Eckert et al. | |
| 5,866,217 A | 2/1999 | Stenoien et al. | |
| 5,902,475 A | 5/1999 | Trozera et al. | |
| 5,925,075 A | 7/1999 | Myers et al. | |
| 5,948,018 A * | 9/1999 | Dereume et al. | 623/1.12 |
| 5,951,599 A | 9/1999 | McCrory | |
| 5,993,489 A | 11/1999 | Lewis et al. | |
| 6,001,123 A | 12/1999 | Lau | |
| 6,010,530 A | 1/2000 | Goicoechea | |
| 6,017,577 A | 1/2000 | Hostettler et al. | |
| 6,024,765 A | 2/2000 | Wallace et al. | |
| 6,027,811 A | 2/2000 | Campbell et al. | |
| 6,033,435 A | 3/2000 | Penn et al. | |
| 6,036,720 A | 3/2000 | Abrams et al. | |
| 6,056,776 A | 5/2000 | Lau et al. | |
| 6,066,167 A | 5/2000 | Lau et al. | |
| 6,139,564 A | 10/2000 | Teoh | |
| 6,140,127 A | 10/2000 | Sprague | |
| 6,168,610 B1 | 1/2001 | Marin et al. | |
| 6,174,328 B1 | 1/2001 | Cragg | |
| 6,217,607 B1 | 4/2001 | Alt | |
| 6,240,616 B1 | 6/2001 | Yan | |
| 6,240,948 B1 | 6/2001 | Hansen, III et al. | |
| 6,248,190 B1 | 6/2001 | Stinson | |
| 6,265,016 B1 | 7/2001 | Hostettler et al. | |
| 6,309,367 B1 | 10/2001 | Boock | |
| 6,312,463 B1 | 11/2001 | Rourke et al. | |
| 6,315,791 B1 | 11/2001 | Gingras et al. | |
| 6,409,754 B1 | 6/2002 | Smith et al. | |
| 6,416,474 B1 | 7/2002 | Penner et al. | |
| 6,451,050 B1 * | 9/2002 | Rudakov et al. | 623/1.15 |
| 6,451,052 B1 | 9/2002 | Burmeister et al. | |
| 6,454,780 B1 | 9/2002 | Wallace | |
| 6,485,507 B1 | 11/2002 | Walak et al. | |
| 6,488,701 B1 | 12/2002 | Nolting et al. | |
| 6,508,832 B1 | 1/2003 | Jalisi et al. | |
| 6,517,571 B1 | 2/2003 | Brauker et al. | |
| 6,527,802 B1 | 3/2003 | Mayer | |
| 6,533,905 B2 | 3/2003 | Johnson et al. | |
| 6,547,815 B2 | 4/2003 | Myers | |
| 6,582,461 B1 | 6/2003 | Burmeister et al. | |
| 6,582,652 B2 | 6/2003 | Craig | |
| 6,613,072 B2 | 9/2003 | Lau et al. | |
| 6,623,520 B2 | 9/2003 | Jalisi | |
| 6,652,574 B1 | 11/2003 | Jayaraman | |
| D484,979 S | 1/2004 | Fontaine | |
| 6,673,108 B2 | 1/2004 | Zilla et al. | |
| 6,676,701 B2 | 1/2004 | Rourke et al. | |
| 6,679,910 B1 | 1/2004 | Granada | |
| 6,695,833 B1 | 2/2004 | Frantzen | |
| 6,695,876 B1 | 2/2004 | Marotta et al. | |
| 6,699,276 B2 | 3/2004 | Sogard et al. | |
| 6,706,061 B1 | 3/2004 | Fischell et al. | |
| 6,719,782 B1 | 4/2004 | Chuter | |
| 6,736,844 B1 | 5/2004 | Glatt et al. | |
| 6,802,851 B2 | 10/2004 | Jones et al. | |
| 6,818,013 B2 | 11/2004 | Mitelberg et al. | |
| 6,821,293 B2 | 11/2004 | Pinchasik | |
| 6,855,154 B2 | 2/2005 | Abdel-Gawwad | |
| 6,899,727 B2 | 5/2005 | Armstrong et al. | |
| 6,936,055 B1 | 8/2005 | Ken et al. | |
| 6,949,116 B2 | 9/2005 | Solymar et al. | |
| 6,979,349 B1 | 12/2005 | Dang et al. | |
| 7,029,493 B2 | 4/2006 | Majercak et al. | |
| 7,041,129 B2 | 5/2006 | Rourke et al. | |
| 7,060,091 B2 | 6/2006 | Killion et al. | |
| 7,105,019 B2 | 9/2006 | Hojeibane | |
| 7,153,322 B2 | 12/2006 | Alt | |
| 7,169,174 B2 | 1/2007 | Fischell et al. | |
| D553,746 S | 10/2007 | Fliedner | |
| D553,747 S | 10/2007 | Fliedner | |
| 7,306,622 B2 | 12/2007 | Jones et al. | |
| 7,311,726 B2 | 12/2007 | Mitelberg et al. | |
| 7,491,226 B2 | 2/2009 | Palmaz et al. | |
| 2002/0035394 A1 | 3/2002 | Fierens et al. | |
| 2002/0042646 A1 | 4/2002 | Wall | |
| 2002/0045931 A1 | 4/2002 | Sogard et al. | |
| 2002/0049495 A1 | 4/2002 | Kutryk et al. | |
| 2002/0065546 A1 | 5/2002 | Machan et al. | |
| 2002/0111543 A1 | 8/2002 | Penner et al. | |
| 2002/0151968 A1 | 10/2002 | Zilla et al. | |
| 2003/0014075 A1 | 1/2003 | Rosenbluth | |
| 2003/0018294 A1 | 1/2003 | Cox | |
| 2003/0060782 A1 | 3/2003 | Bose et al. | |
| 2003/0060871 A1 | 3/2003 | Hill et al. | |
| 2003/0074053 A1 | 4/2003 | Palmaz et al. | |
| 2003/0093111 A1 | 5/2003 | Ken et al. | |
| 2003/0100945 A1 | 5/2003 | Yodfat et al. | |
| 2003/0124279 A1 | 7/2003 | Sridharan et al. | |
| 2003/0171801 A1 | 9/2003 | Bates | |
| 2003/0229286 A1 | 12/2003 | Lenker | |
| 2003/0229393 A1 | 12/2003 | Kutryk et al. | |
| 2003/0233141 A1 | 12/2003 | Israel | |
| 2004/0029268 A1 | 2/2004 | Colb et al. | |
| 2004/0087998 A1 | 5/2004 | Lee et al. | |
| 2004/0116998 A1 | 6/2004 | Erbel et al. | |
| 2004/0170685 A1 | 9/2004 | Carpenter et al. | |
| 2004/0172121 A1 | 9/2004 | Eidenschink et al. | |
| 2004/0186562 A1 | 9/2004 | Cox | |
| 2004/0193206 A1 | 9/2004 | Gerberding et al. | |
| 2005/0008869 A1 | 1/2005 | Clark et al. | |
| 2005/0043787 A1 | 2/2005 | Kutryk et al. | |
| 2005/0075716 A1 | 4/2005 | Yan | |
| 2005/0090888 A1 * | 4/2005 | Hines et al. | 623/1.11 |
| 2005/0096725 A1 | 5/2005 | Pomeranz et al. | |
| 2005/0124896 A1 | 6/2005 | Richter et al. | |
| 2005/0137677 A1 | 6/2005 | Rush | |
| 2005/0137680 A1 | 6/2005 | Ortiz et al. | |
| 2005/0154448 A1 | 7/2005 | Cully et al. | |
| 2005/0171593 A1 | 8/2005 | Whirley et al. | |
| 2005/0267568 A1 | 12/2005 | Berez et al. | |
| 2005/0283220 A1 | 12/2005 | Gobran et al. | |
| 2006/0020322 A1 | 1/2006 | Leynov et al. | |
| 2006/0036308 A1 | 2/2006 | Goshgarian | |
| 2006/0036311 A1 * | 2/2006 | Nakayama et al. | 623/1.15 |
| 2006/0106421 A1 | 5/2006 | Teoh | |
| 2006/0121080 A1 | 6/2006 | Lye et al. | |
| 2006/0136037 A1 | 6/2006 | DeBeer et al. | |
| 2006/0142849 A1 | 6/2006 | Killion et al. | |
| 2006/0149355 A1 | 7/2006 | Mitelberg et al. | |
| 2006/0155355 A1 | 7/2006 | Jung | |
| 2006/0173530 A1 | 8/2006 | Das | |
| 2006/0200230 A1 | 9/2006 | Richter | |
| 2006/0200234 A1 | 9/2006 | Hines | |
| 2006/0206199 A1 | 9/2006 | Churchwell et al. | |
| 2006/0217799 A1 | 9/2006 | Mailander et al. | |
| 2006/0224237 A1 | 10/2006 | Furst et al. | |
| 2006/0259123 A1 | 11/2006 | Dorn | |
| 2006/0265051 A1 | 11/2006 | Caro et al. | |
| 2006/0276877 A1 | 12/2006 | Owens et al. | |

| | | | |
|---|---|---|---|
| 2006/0276878 A1 | 12/2006 | Owens et al. | |
| 2006/0276879 A1 | 12/2006 | Lye et al. | |
| 2006/0287710 A1 | 12/2006 | Lendlein et al. | |
| 2007/0038288 A1 | 2/2007 | Lye et al. | |
| 2007/0083258 A1 | 4/2007 | Falotico et al. | |
| 2007/0088387 A1 | 4/2007 | Eskridge et al. | |
| 2007/0112415 A1 | 5/2007 | Bartlett | |
| 2007/0213800 A1 | 9/2007 | Fierens et al. | |
| 2007/0276477 A1 | 11/2007 | Lee et al. | |
| 2007/0288083 A1 | 12/2007 | Hines | |
| 2008/0004653 A1 | 1/2008 | Sherman et al. | |
| 2009/0054966 A1 | 2/2009 | Rudakov et al. | |
| 2009/0132022 A1 | 5/2009 | Banas | |

FOREIGN PATENT DOCUMENTS

| | | |
|---|---|---|
| EP | 0 864 301 | 9/1998 |
| EP | 0947204 | 10/1999 |
| EP | 1 086 663 | 3/2001 |
| EP | 1121911 | 8/2001 |
| EP | 1129666 | 9/2001 |
| EP | 1391184 | 2/2004 |
| EP | 1 470 795 | 10/2004 |
| EP | 1543798 | 6/2005 |
| EP | 1550477 | 7/2005 |
| EP | 1797844 | 6/2007 |
| JP | 1254623 | 10/1989 |
| JP | 11-506034 | 6/1999 |
| JP | 11299901 A * | 11/1999 |
| JP | 2002-516706 | 6/2002 |
| JP | 2002-529193 | 9/2002 |
| WO | WO 97/17913 | 5/1997 |
| WO | WO 98/14137 | 4/1998 |
| WO | WO 99-02092 | 1/1999 |
| WO | WO 99-58084 | 11/1999 |
| WO | WO 99/62432 | 12/1999 |
| WO | WO 99-62432 | 12/1999 |
| WO | WO 00/01308 | 1/2000 |
| WO | WO 00-06145 | 2/2000 |
| WO | WO 00/28922 | 5/2000 |
| WO | WO 00-47134 | 8/2000 |
| WO | WO 00/48517 | 8/2000 |
| WO | WO 00-51522 | 9/2000 |
| WO | WO-00-56247 | 9/2000 |
| WO | WO 01/03607 | 1/2001 |
| WO | WO 01-66167 | 9/2001 |
| WO | WO 01-87184 | 11/2001 |
| WO | WO 01-93782 | 12/2001 |
| WO | WO 02-22024 | 3/2002 |
| WO | WO 02-051336 | 7/2002 |
| WO | WO-02-069783 | 9/2002 |
| WO | WO 02/078764 | 10/2002 |
| WO | WO 03/026713 | 4/2003 |
| WO | WO 03-049600 | 6/2003 |
| WO | WO 03-049600 | 6/2003 |
| WO | WO 03/065881 | 8/2003 |
| WO | WO 2004-000379 | 12/2003 |
| WO | WO 2004-028405 | 4/2004 |
| WO | WO 2005/000165 | 1/2005 |
| WO | WO 2005-065580 | 7/2005 |
| WO | WO 2005-086831 | 9/2005 |
| WO | WO-2005-094725 | 10/2005 |
| WO | WO 2005-094726 | 10/2005 |
| WO | WO 2005/094726 | 10/2005 |
| WO | WO-2006-033641 | 3/2006 |

OTHER PUBLICATIONS

Reul, J. et al., Long-Term Angiographic and Histopathalogic Findings in Experimental Aneurysms of the Carotid Bifurcation Embolized with Platinum and Tungsten Coils, American Journal of Neuroradiology, Jan. 1997, pp. 35-42, vol. 18.

* cited by examiner

| Dimensions | As manufactured | Crimped | Expanded |
|---|---|---|---|
| Strut thickness | 0.003" (0.076mm) | | |
| Outer Diameter | 0.080" (2.03mm) | 0.040" (1.02mm) | 4.0mm |
| Distance between struts | 0.80mm | 0.40mm | 2mm |

MEDICAL DEVICE

CROSS REFERENCES TO RELATED APPLICATIONS

This is a continuation-in-part application from U.S. patent application Ser. No. 10/580,139 filed on May 19, 2006, which claims priority from International Patent Application No. PCT/SG2004/000407 filed on Dec. 13, 2004, which claims priority from Singapore Patent Application No. 200401735-6 filed on Mar. 31, 2004.

FIELD OF THE INVENTION

The present invention relates to a medical device for insertion into a bodily vessel to treat an aneurysm.

BACKGROUND OF THE INVENTION

Vascular diseases include aneurysms causing hemorrhage, atherosclerosis causing the occlusion of blood vessels, vascular malformation and tumors. Vessel occlusion or rupture of an aneurysm within the brain causes of stroke. Aneurysms fed by intracranial arteries can grow within the brain to a point where their mass and size can cause a stroke or the symptoms of stroke, requiring surgery for removal of the aneurysms or other remedial intervention.

Occlusion of coronary arteries, for example, is a common cause of heart attack. Diseased and obstructed coronary arteries can restrict the flow of blood in the heart and cause tissue ischemia and necrosis. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Conventional open-heart surgery is, of course, very invasive and traumatic for patients undergoing such treatment. Therefore, alternative methods being less traumatic are highly desirable.

One of the alternative methods is balloon angioplasty that is a technique in which a folded balloon is inserted into a stenosis, which occludes or partially occludes an artery and is inflated to open the occluded artery. Another alternative method is atherectomy that is a technique in which occlusive atheromas are cut from the inner surface of the arteries. Both methods suffer from reocclusion with certain percentage of patients.

A recent preferred therapy for vascular occlusions is placement of an expandable metal wire-frame including a stent, within the occluded region of blood vessel to hold it open. The stent is delivered to the desired location within a vascular system by a delivery means, usually a catheter. Advantages of the stent placement method over conventional vascular surgery include obviating the need for surgically exposing, removing, replacing, or by-passing the defective blood vessel, including heart-lung by-pass, opening the chest, and general anaesthesia.

When inserted and deployed in a vessel, duct or tract ("vessel") of the body, for example, a coronary artery after dilatation of the artery by balloon angioplasty, a stent acts as a prosthesis to maintain the vessel open. The stent usually has an open-ended tubular form with interconnected struts as its sidewall to enable its expansion from a first outside diameter which is sufficiently small to allow the stent to traverse the vessel to reach a site where it is to be deployed, to a second outside diameter sufficiently large to engage the inner lining of the vessel for retention at the site. A stent is typically delivered in an unexpaded state to a desired location in a body lumen and then expanded. The stent is expanded via the use of a mechanical device such as a balloon, or the stent is self-expanding.

Usually a suitable stent for successful interventional placement should possess features of relatively non-allergenic reaction, good radiopacity, freedom from distortion on magnetic resonance imaging (MRI), flexibility with suitable elasticity to be plastically deformable, strong resistance to vessel recoil, sufficient thinness to minimize obstruction to flow of blood (or other fluid or material in vessels other than the cardiovascular system), and biocompatibility to avoid of vessel re-occlusion. Selection of the material of which a stent is composed, as well as design of the stent, plays an important role in influencing these features.

Furthermore, implantable medical devices have been utilized for delivery of drugs or bioreagents for different biological applications. Typically, the drugs or bioreagents are coated onto the surfaces of the implantable medical devices or mixed within polymeric materials that are coated onto the surfaces of the implantable medical devices. However, all the current available methods suffer from one or more problems including uncontrollable release, form limitations of drugs, and bulky appearance.

Therefore, there is desire for an implantable medical device that is able to deliver drugs or reagents efficiently to the endovascular system, especially intracranial blood vessels.

A method for treating bifurcation and trifurcation aneurysms is disclosed in the previously filed cross-related application entitled "A Method for Treating Aneurysms", the contents of which are herein incorporated by reference.

SUMMARY OF THE INVENTION

In a first preferred aspect, there is provided a method for treating a bifurcation or trifurcation aneurysm occurring on a first artery, the first artery and a second artery joining to a third artery, the method comprising:
  inserting a medical device such that it is at least partially located in the first artery and is at least partially located in the third artery;
  expanding the medical device from a first position to a second position, said medical device is expanded radially outwardly to the second position such that the exterior surface of said medical device engages with the inner surface of the first and third arteries so as to maintain a fluid pathway through said arteries; and
  positioning the medical device such that a membrane of the medical device is located against an aneurysm neck of the aneurysm to obstruct blood circulation to the aneurysm when the medical device is expanded to the second position, and at least a portion of the membrane is secured to the medical device to maintain the position of the membrane relative to the medical device when expanded to the second position;
  wherein the membrane is permeable and porous, the size of the pores of the membrane and the ratio of the material surface area of the membrane being such that blood supply to perforators and/or microscopic branches of main brain arteries is permitted to improve healing of the first artery but blood supply to the aneurysm is prevented.

The medical device may be inserted such that blood circulation to the second artery is unobstructed by the membrane.

The distance between adjacent pores may be from about 40 to 100 microns.

The membrane may be made of a biocompatible and elastomeric polymer.

The membrane may have a thickness of about 0.0005 to 0.005".

The ratio of the material surface area of the membrane may be from about 25 to 75%.

The membrane may have pores between 20 to 100 microns in size.

The membrane may be made from polymeric material or biodegradable material.

The biodegradable material may form multiple sub-layers mixed with drugs or reagents.

The at least one reagent may be any one form selected from the group consisting of: solid tablet, liquid and powder.

The membrane may be capable of isotropic expansion.

The membrane may be disposed on the exterior surface of the device.

The membrane may circumferentially surround a portion of the device.

The membrane may cover a portion of the device.

The membrane may have fabricated pores between 20 to 100 microns in size.

The pores may be fabricated by laser drilling.

The distance between the pores may be less than 100 μm.

The membrane may comprise a plurality of polymeric strips secured to the medical device.

The strips may be less than 0.075 mm and the distance between adjacent strips is less than 100 μm.

The membrane may comprise a mesh secured to the medical device.

Spaces of the mesh may be less than 100 μm and the width of the meshing is between 0.025 to 0.050 mm.

The aneurysm may be any one from the group consisting of: a regular size, giant or wide neck aneurysm having an aneurysm neck greater than 4 millimeters or a dome to neck ratio greater than 2, berry aneurysm, CC fistula and fusiform aneurysm.

The medical device may comprise a generally tubular structure having an exterior surface defined by a plurality of interconnected struts having interstitial spaces therebetween.

The medical device may be self-expandable or balloon expandable.

The membrane may be supported by the generally tubular structure and is attached to at least one strut.

The medical device may be a stent.

The membrane may be tubular having a diameter similar to a nominal initial diameter of the stent; and wherein the membrane is disposed onto the outer surface of the stent or introduced by dip coating or spraying between the struts of the stent.

The membrane may be a segment of a tubular structure disposed onto a portion of the outer surface of the stent.

The membrane may substantially cover the entire circumferential surface of the medical device.

The permeability and porosity of the membrane may alter the hemodynamics of the aneurysm sac of the aneurysm to initiate intra-aneurysmal thrombosis.

BRIEF DESCRIPTION OF THE DRAWINGS

An example of the invention will now be described with reference to the accompanying drawings, in which.

DETAILED DESCRIPTION OF THE DRAWINGS

Implantable medical devices include physical structures for delivering drugs or reagents to desired sites within the endovascular system of a human body. Implantable medical devices may take up diversified shapes and configurations depending upon specific applications. Common implantable medical devices include stents, vena cava filters, grafts and aneurysm coils. While stents are described, it is noted that the disclosed structures and methods are applicable to all the other implantable medical devices.

The endovascular system of a human body includes blood vessels, cerebral circulation system, tracheo-bronchial system, the biliary hepatic system, the esophageal bowel system, and the urinary tract system. Although exemplary stents implantable 202 in blood vessels are described, they are applicable to the remaining endovascular system.

Stents 202 are expandable prostheses employed to maintain vascular and endoluminal ducts or tracts of the human body open and unoccluded, such as a portion of the lumen of a coronary artery after dilatation of the artery by balloon angioplasty. A typical stent 202 is a generally tubular structure having an exterior surface defined by a plurality of interconnected struts having interstitial spaces there between. The generally tubular structure is expandable from a first position, wherein the stent is sized for intravascular insertion, to a second position, wherein at least a portion of the exterior surface of the stent contacts the vessel wall. The expanding of the stent is accommodated by flexing and bending of the interconnected struts throughout the generally tubular structure. It is contemplated that many different stent designs can be produced. A myriad of strut patterns are known for achieving various design goals such as enhancing strength, maximizing the expansion ratio or coverage area, enhancing longitudinal flexibility or longitudinal stability upon expansion, etc. One pattern may be selected over another in an effort to optimize those parameters that are of particular importance for a particular application.

Figure 1A:
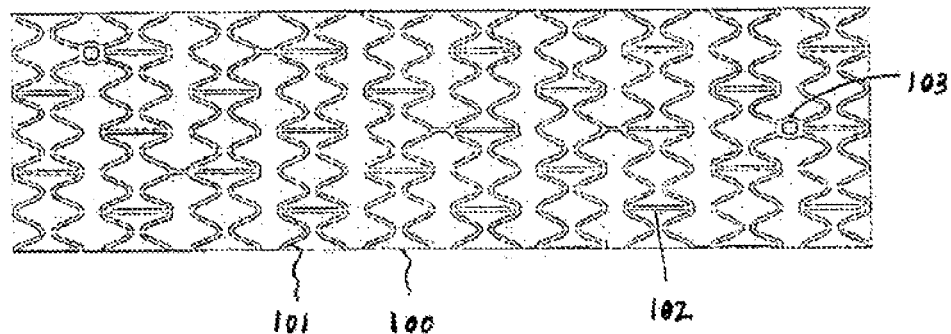
FIGS. 1A and 1B are two exemplary balloon expandable stents.
Figure 1B:
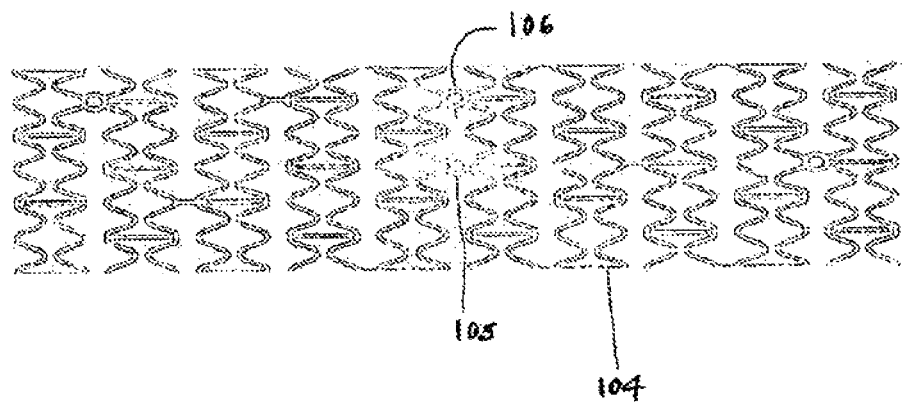

Referring to FIGS. 1A and 1B, there are provided two exemplary balloon expandable stent designs. FIG. 1A shows a tubular balloon expandable stent 100 with end markers 103 to increase visibility of the stent 100. The stent 100 is composed of stent struts of a ring 101, ring connectors 102, and end markers 103.

Referring to FIG. 1A, the stents 100 are made of multiple circumstantial rings 101, where the ring connectors 102 connect two or three adjacent rings 101 to hold the rings in place. For the end markers 103, FIG. 1A shows a "disc" shaped marker. Actually, the shape is not critical so long that the marker can be used to increase further visibility to the stents 100. FIG. 1B shows a tubular balloon expandable stent 104 which is similar to the stent 100 as shown in FIG. 1A except that the stent 104 comprises of center markers 105, 106. The center markers 105, 106 help to locate an aneurysm opening during an implantation operation. The center markers 105, 106 can be of the same material and shape as the end markers 103.

Figure 2:
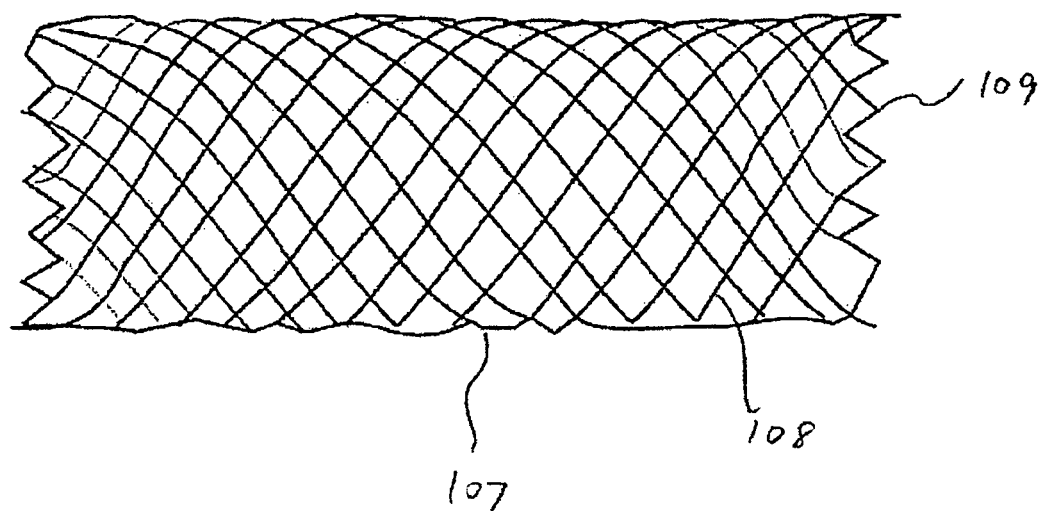
FIG. 2 shows a self-expanding stent.

Referring to FIG. 2, there is provided a self-expanding stent 107 that is made of wires/ribbons. While a self-expanding stent may have many designs, FIG. 2 shows the stent 107 having a typical braided pattern 108 with welded ends 109. The stent 107 is so designed that is relatively flexible along its longitudinal axis to facilitate delivery through tortuous body lumens, but that is stiff and stable enough radially in an expanded condition to maintain the patency of a body lumen, such as an artery when implanted therein.

Figure 4:
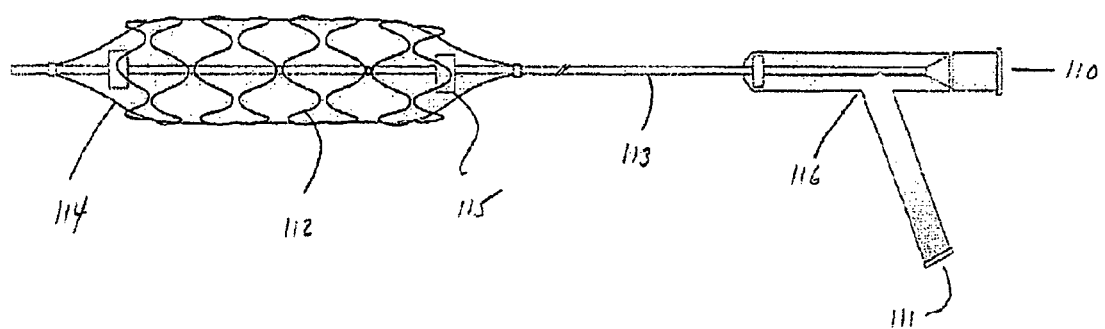
FIG. 4 shows a delivery system with a stent expanded onto the balloon.

Turning to FIG. 4, it is shown an expanded tubular stent 112. When the tubular stent 112 is fully expanded to its deployed diameter, the latticework of struts takes on a shape in which adjacent crests undergo wide separation, and portions of the struts take on a transverse, almost fully lateral orientation relative to the longitudinal axis of the stent. Such lateral orientation of a plurality of the struts enables each fully opened cell to contribute to the firm mechanical support offered by the stent in its fully deployed condition, to assure a rigid structure which is highly resistant to recoil of the vessel wall following stent deployment.

While a stent 112 may be deployed by radial expansion under outwardly directed radial pressure exerted, for example, by active inflation of a balloon of a balloon catheter on which the stent is mounted, the stent 112 may be self-expandable. In some instances, passive spring characteristics of a preformed elastic (i.e., self-opening) stent serve the purpose. The stent is thus expanded to engage the inner lining or inwardly facing surface of the vessel wall with sufficient resilience to allow some contraction but also with sufficient stiffness to largely resist the natural recoil of the vessel wall.

In one embodiment, the implantable medical devices are intracranial stents 202 and delivery systems for stenotic lesions and aneurysms 201. Due to the characteristics of intracranial blood vessels, the intracranial stents 202 are designed to be very flexible, low profile (0.033"-0.034" or even less as crimped onto delivery catheter) and thin wall (0.0027"-0.0028"). The intracranial stents 202 do not necessarily have the highest possible radial strength because there is no need of high strength for intracranial applications. The radiopacity of the intracranial stents may be provided by either including radiopaque markers 205 made from gold or platinum or making the stents 202 from platinum/iridium/tungsten alloys. Stents 202 for treating aneurysms 201 have a special type of platinum "star markers" 204 in the middle of their bodies to assist in precise indication and alignment of the stents 202 over the aneurysm neck 201 and allow further operation with aneurysms 201.

Figure 3A:
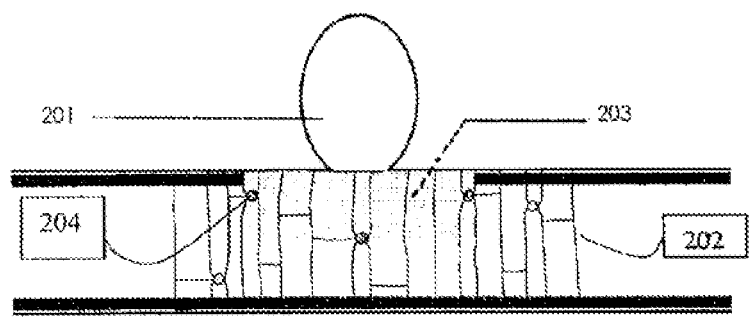
FIG. 3A is diagrammatic view of a stent disposed in the location of an aneurysm.
Figure 3B:
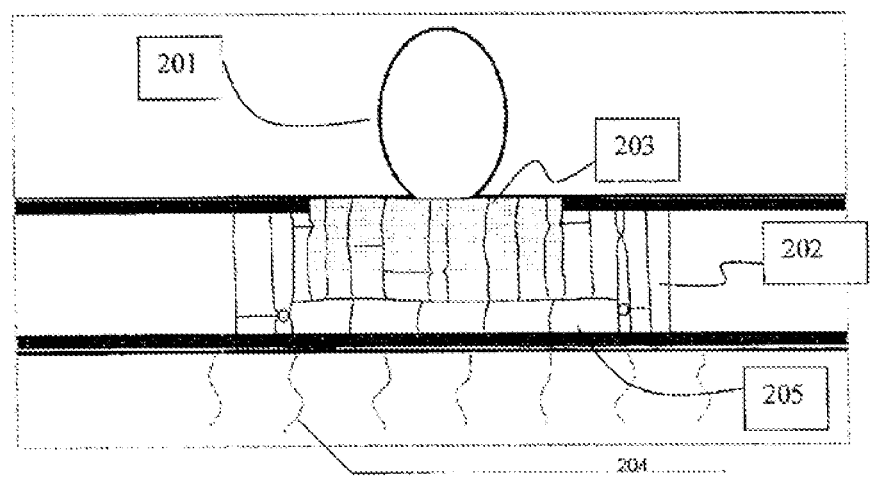
FIG. 3B is diagrammatic view as FIG. 3A except that a port of the stent is formed of opened cells.

As shown in FIG. 3A, the intracranial stent 202 is disposed in the location of an aneurysm 201. The membrane 203 partially covers the stent 202 and is positioned to seal the neck of the aneurysm 201. The radiopaque markers 204 are located in the middle of the stent 202 to provide visibility of the stent 202 during operation and post-operation inspection. Referring to FIG. 3B, a portion of the stent 202 is formed of opened cells 205. This design avoids blocking perforators. The perforators refer to small capillary vessels that have important and distinctive blood supply functions. It is possible that tubular stents can block perforators and inhibit important functions.

Referring to FIG. 4, the delivery system includes a guide wire lumen 110, a balloon inflating lumen 111, a connector 116, a balloon catheter shaft 113, and platinum marker bands 115 on the catheter shaft 113. The guide wire lumen 110 is used for introducing a guide wire in a balloon catheter, and the balloon inflating lumen 111 for inflating the balloon after the stent to be placed reaches its targeted location. The connector 116 is used for separating the guide wire lumen 110 and the balloon inflating lumen 111. The balloon catheter shaft 113 carries the guide wire lumen 110 and the balloon inflating lumen 111 separately, with a typical length of about 135-170 cm. The ring markers 115 on the catheter shaft 113 are used for showing the start of balloon tapers and the edges of the stent. In FIG. 3, an expanded stent 112 is shown being mounted onto an expanded balloon. The delivery catheter can be essentially a conventional balloon dilatation catheter used for angioplasty procedures. The balloon may be formed of suitable materials such as irradiated polyethylene, polyethylene terephthalate, polyvinylchloride, nylon, and copolymer nylons such as Pebax™. Other polymers may also be used. In order for the stent to remain in place on the balloon during delivery to the desired site within an artery, the stent is crimped onto the balloon.

In a preferred embodiment, the delivery of the stent is accomplished in the following manner. The stent is first mounted onto the inflatable balloon on the distal extremity of the delivery catheter. Stent is mechanically crimped onto the exterior of the folded balloon. The catheter/stent assembly is introduced within vasculature through a guiding catheter. A guide wire is disposed across the diseased arterial section and then the catheter/stent assembly is advanced over a guide wire within the artery until the stent is directly under the diseased lining. The balloon of the catheter is expanded, expanding the stent against the artery. The expanded stent serves to hold open the artery after the catheter is withdrawn. Due to the formation of the stent from an elongated tube, the undulating component of the cylindrical elements of the stent is relatively flat in transverse cross-section, so that when the stent is expanded, the cylindrical elements are pressed into the wall of the artery and as a result do not interfere with the blood flow through the artery. The cylindrical elements of the stent which are pressed into the wall of the artery will eventually be covered with endothelial cell layer which further minimizes blood flow interference. Furthermore, the closely spaced cylindrical elements at regular intervals provide uniform support for the wall of the artery, and consequently are well adopted to tack up and hold in place small flaps or dissections in the wall of the artery.

For resilient or self-expanding prostheses, they can be deployed without dilation balloons. Self-expanding stents can be pre-selected according to the diameter of the blood vessel or other intended fixation site. While their deployment requires skill in stent positioning, such deployment does not require the additional skill of carefully dilating the balloon to plastically expand the prosthesis to the appropriate diameter. Further, the self-expanding stent remains at least slightly elastically compressed after fixation, and thus has a restoring force which facilitates acute fixation. By contrast, a plastically expanded stent must rely on the restoring force of deformed tissue, or on hooks, barbs, or other independent fixation elements.

The presence of a stent in a vessel tends to promote thrombus formation as blood flows through the vessel, which results in an acute blockage. In addition, as the outward facing surface of the stent in contact or engagement with the inner lining of the vessel, tissue irritation can exacerbate restenosis attributable to hyperplasia. Moreover, it is desirable to deliver drugs or reagents into the aneurysms to enhance the blockage of blood flow into the aneurysms. Finally, implantable medical devices have been used as vehicles to deliver drugs or reagents to specific locations within the vascular system of a human body.

In one example, an intracranial stent 202 is specially designed for low pressure deployment. The stent 202 has adequate radial strength for targeting a specific environment of fragile intracranial vessel. The stent 202 is designed to allow for delivering high stent performance and absolutely conforming longitudinal flexibility.

Low pressure deployment of a stent is defined as a pressure equal to or below 4 atm. This level of pressure enables the stent 202 to be fully deployed to support a stenosed intracranial vessel or aneurysm neck 201 without introducing trauma or rapture of a target vessel. The stent 202 can be deployed using balloon techniques or be self-expandable.

The stent 202 comprises structural elements that restrict potential over expansion, matching the inner diameter of the vessel and to make deployment extremely precise. This feature of the structural elements in combination with low pressure deployment potentially reduces vessel injury, rupture or restenosis.

The stent 202 also has longitudinal flexibility equal to or better than what is provided by a delivery catheter. This means that the stent does not add increased rigidity to the device. The trackability of the stent 202 depends on the mechanical properties of the catheter and is not restricted by stent 202 alone. The longitudinal flexibility of the stent 202 can be measured by force in grams to deflect the stent from neutral line. This force brings stent deflection to 1 mm for less than 8 grams. Existing catheters can provide 20-22 grams per 1 mm deflection. This condition is also extremely important when creating stent compliance to particular vessels and saves the vessel from possible traumatic reaction.

The structure of the stent 202 is designed to provide a normalized radial force of 18-19 grams/mm of length and may reach values close to the ones found in existing coronary stents. Stent structural support provides 3-4% of deflection of the stent structure together with intracranial vessel wall natural pulsing. This leads to greater stent conformity and a reduced vessel injury score.

The intracranial stent 202 has profile in compressed delivery mode 0.020".

The intracranial stent 202 is designed to be compressed onto delivery catheter with a profile as low 0.014"-0.016" having stent profile 0.020"-0.022".

The intracranial stent 202 has even material distribution and wall coverage, creating needed vessel support. The material ratio is in the range of 10-17% depending on deployment diameter.

The intracranial stent 202 has a strut thickness and width not larger than 0.0028". Strut dimensions are selected which make the least intrusive stent material volume and to reduce the vessel injury score.

The stent surface to length ratio is set to be 1.1-1.3 $mm^2$/mm to provide minimal vessel injury score.

At least one membrane 203 is disposed onto the outer surface of a stent 202. The membrane 203 comprises pockets which serve as receptacles for drugs or reagents to deliver the drugs or reagents into vascular systems. The membrane 203 covers a part of a stent 202 as shown in FIGS. 3A and 3B, wherein the size of the membrane 203 is variable depending on application. In one example, the membrane 203 covers the whole outer surface of a stent 202. Thus, the membrane 203 may be in any shape or size.

Figure 5:
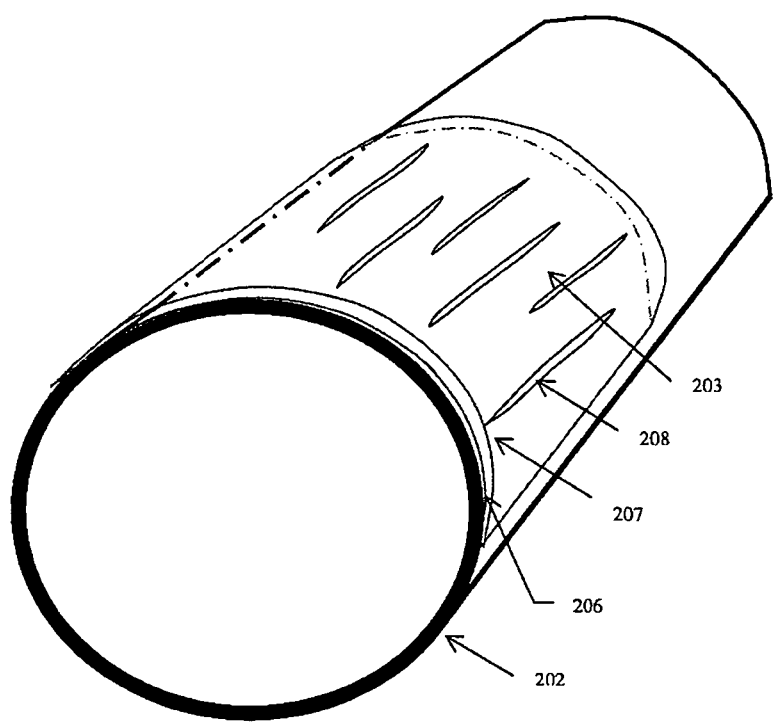
FIG. 5 is diagrammatic view of a stent partially covered by a membrane with pockets.

In certain embodiments, the membrane 203 comprises a first layer attached to the outer surface of an implantable medical device such as a stent 202. An intermediate layer is attached to the first layer wherein the intermediate layer comprises at least two circumferential strips being separated from each other and a second layer covering the first layer and the intermediate layer. The spaces surrounded by the first layer, the circumferential strips and the second layer form the pockets that serve as receptacles for drugs or reagents. In other embodiments, the intermediate layer includes at least one opening so that the pockets can be formed within the openings. The shapes and sizes of the openings may vary in accordance with specific applications. As shown in FIG. 5, a stent 202 is partially covered by a membrane 203 that comprises a first layer 206 and a second layer 207. FIG. 5 also shows the drug releasing pores 208.

Many polymeric materials are suitable for making the layers of the membrane 203. Typically, one first layer is disposed onto the outer surface of a stent. The first layer has a thickness of 0.002"-0.005" with pore sizes of 20-30 microns and similar to nominal initial diameter.

In certain embodiments, the first layer serves as an independent membrane 203 to mechanically cover and seal aneurysms 201. In certain embodiments, the first and/or second layers can be comprised of biodegradable material as a drug or reagent carrier for sustained release.

It is desirable that the intermediate layer be formed of a material which can fuse to the first and second layers or attached to the first layer in a different manner. In certain embodiments, the intermediate layer may be merged with the first layer to form a single layer with recessions within the outer surface of the merged layer.

The second and intermediate layers can be made of biodegradable material that contains drugs or reagents for immediate or sustained controlled release. After biodegradable material is gone through the degradation process, the membrane 203 is still in tact providing vessel support.

The second layer may be composed of a polymeric material. In preferred embodiments, the second layer has a preferable thickness of about 0.001" with pore sizes of about 70-100 microns.

The polymeric layers may also be formed from a material selected from the group consisting of fluoropolymers, polyimides, silicones, polyurethanes, polyurethanes ethers, polyurethane esters, polyurethaneureas and mixtures and copolymers thereof. Biodegradable polymeric materials can also be used.

The fusible polymeric layers may be bonded by adhering, laminating, or suturing. The fusion of the polymeric layers may be achieved by various techniques such as heat-sealing, solvent bonding, adhesive bonding or use of coatings.

Types of drugs or reagents that may prove beneficial include substances that reduce the thrombogenic, inflammatory or smooth muscle cell proliferative response of the vessel to the implantable medical devices. For example, cell inhibitors can be delivered in order to inhibit smooth muscle cells proliferation. In intracranial or some other applications fibrin sealants can be used and delivered to seal aneurysm neck and provide fibroblasts and endothelial cells growth. Specific examples of drugs or reagents may include heparin, phosporylcholine, albumin, dexamethasone, paclitaxel and vascular endothelial growth factor (VEGF).

The drug or reagents can be incorporated into the implantable medical devices in various ways. For example the drug or reagent can be injected in the form of a gel, liquid or powder into receptacles of the pockets. Alternatively the drug or reagent can be supplied in a powder which has been formed into a solid tablet positioned in the receptacles.

Another prerequisite of a successful treatment of these extremely small diameter vessels is that the stent delivery system is highly flexible to allow it to be advanced along the anatomy of the cerebral circulation. In addition, the total stent delivery system must be of extremely small profile, to treat diseased intra-cranial arteries generally ranging from 1.5 mm to 5 mm.

Figure 6:
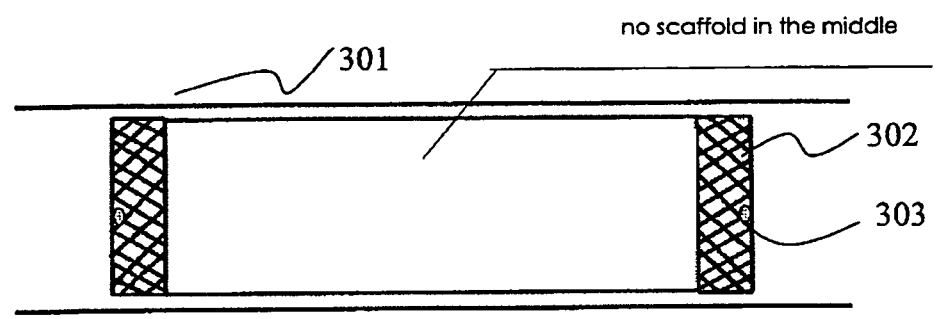
FIG. 6 is a cross-sectional view of a sleeve as a membrane supported by two ring-like stents.

Referring to FIG. 6, in certain embodiments a membrane 203 is embodied as a sleeve 301 supported by two ring-like short stents 302 at both ends of a device so that the membrane 203 covers the whole area of the device 302. There is no scaffold support in the middle of the device 302. Radiopaque markers 303 are located at both ends of the stent 302. Depending on applications, the rings are balloon expandable and made from stainless steel or self-expandable made from NiTi (memory shaped nickel-titanium alloy).

The membrane 203 is part of a hemorrhagic stent structure designed to effectively occlude aneurysm neck and "recanalize" the vessel. It'll allow rebuilding vessel and essentially eliminating aneurysm. No need of expensive (and extra-traumatic, sometimes too massive) coiling is expected.

This device is a preferable solution to treat: giant and wide neck aneurysms, bifurcation and trifurcation aneurysms. It is also a preferred treatment solution for cc fistula ruptured in cavernous sinus, pseudoaneurysms, saccular aneurysms.

The membrane 203 is elastic to allow its own expansion five to six times without disintegration and detachment from the stent structure. The thickness of the membrane 203 is expected to be not more than 0.002" in crimped position and 0.001" in expanded form. The mechanical properties do not introduce extra rigidity to the intracranial stent 202 and have no resistance to stent expansion. The membrane material also allows an expanded membrane 203 to endure normal blood pressure.

The membrane 203 is not solid, but is formed as strips between stent struts, or with a series of holes or ovals. The membrane 203 therefore could be porous, or woven mesh. The membrane 203 could also be designed and structured in a way such that there is a system of holes to allow blood penetration into the system of perforators and not allow it into the aneurysm 201.

For upper brain arteries above Siphon, a porous and permeable membrane 203 is ideal. Such a membrane 203 treat an aneurysm neck 201 without blocking microvessels (perforators). It is expected that interventional neuroradiologists (INRs) to be more willing to use the membrane 203 than other known techniques for dealing with aneurysm necks 201. The permeable membrane 203 has a system of holes or pores with borders between them not larger than 100 microns. The holes or pores may range between 50 to 100 microns. The membrane 203 is able to significantly improve hemodynamics around the aneurysm 201, since it has a lower delivery profile and is more flexible compared to a stent 202 with a solid membrane.

The membrane 203 is attached to the stent struts. The membrane 203 may be attached using spraying, a dipping technique or heat bonding to the intermediate polymeric layer. The stent 202 is placed on a mandrel (hard PTFE or metal), or hung on a hook and the PU solution is sprayed and solidified with a quick drying process. Alternatively, the stent 202 is placed on the mandrel or on the hook and submerged into a PU solution.

A biodegradable membrane 203 enables drug delivery and is later dissolved. There are applications where there is no need for a membrane 203 to exist after exceeding 15 to 20 days after placement and thus the membrane 203 could be dissolved.

The membrane 203 may be made from PU, Silicon, or any other elastomeric medical grade polymer.

Figure 7:
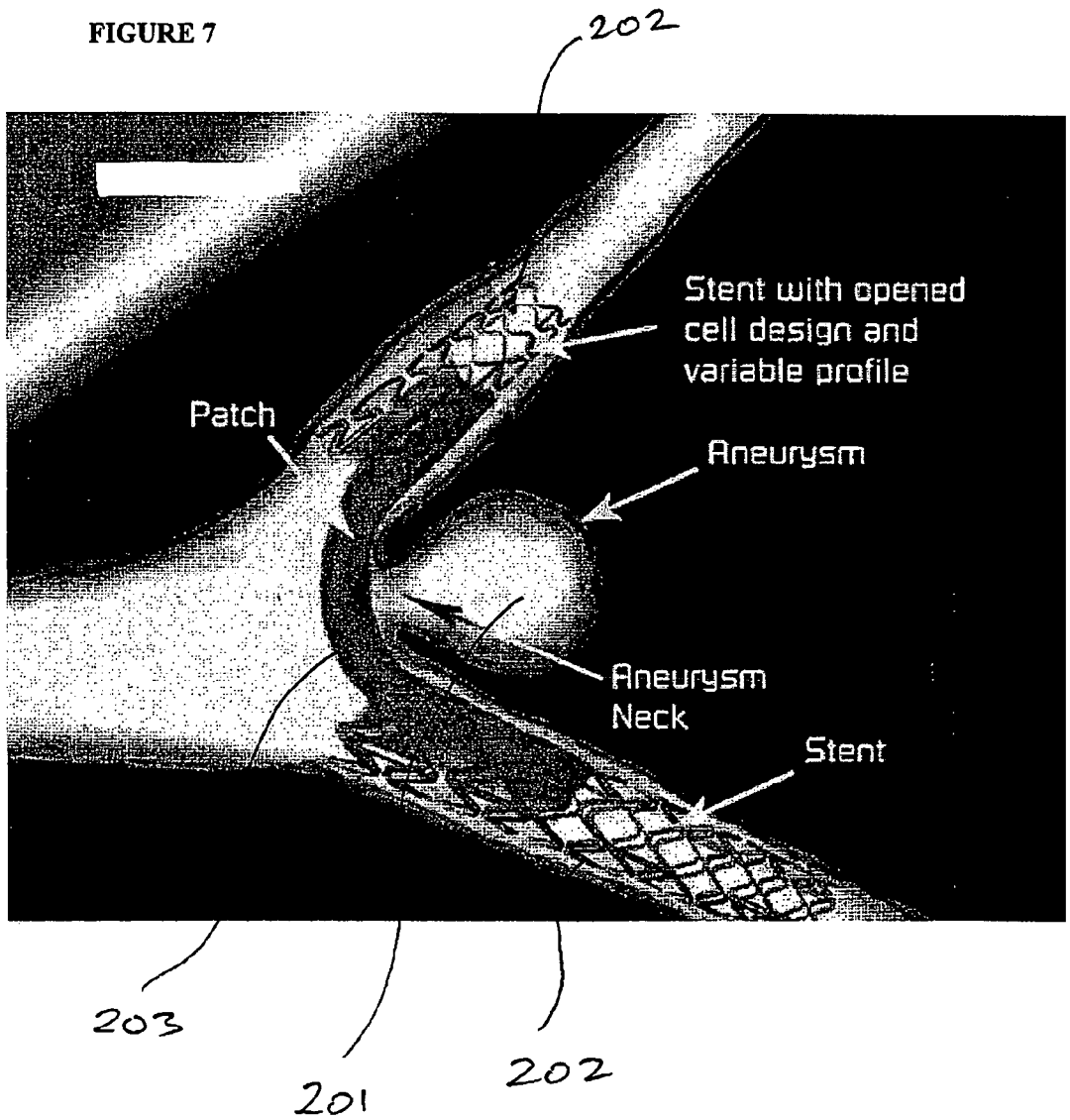
FIG. 7 is a diagrammatic view of a membrane joining two stents for treating a bifurcation aneurysm.

Referring to FIG. 7, a membrane 203 for bifurcational stents 202 to treat a bifurcation or trifurcation aneurysm 201 is provided. At least 30 to 35% of aneurysms are located at bifurcation sites of intracranial vessels. This membrane 203 is one-sided and non-circumferential. The bifurcation stents 202 are joined by a membrane 203 to cover the aneurysm neck 201. The same pattern can be applicable to self-expandable (super-elastic) or balloon expandable (stainless steel, CoCr, Ptlr alloys) stents 202.

Figures 8, 9:
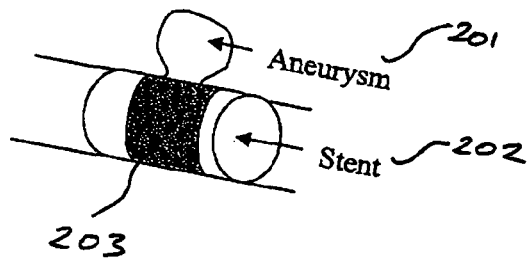
FIG. 8 is a diagrammatic view of an aneurysm covered with the membrane of a stent to obstruct blood circulation to the aneurysm.
FIG. 9 is a table of typical dimensions for the stent.

Referring to FIG. 8, an aneurysm 201 is covered with the membrane 203 of an intracranial stent 202 to treat and prevent ischemic and hemorrhagic stroke. The intracranial stent 202 coupled with a membrane 203 acts as a scaffold to open clogged arteries, and as a cover to prevent blood circulation to the aneurysm 201. Obstructing blood supply to the aneurysm 201 isolates the aneurysm 201 from normal blood circulation, and thereby eventually causes it to dry out. Complete obstruction to the aneurysm 201 may not be necessary.

FIG. 9 provides a table with typical dimensions for the intracranial stent 202 for use with the membrane 203. The material for the membrane 203 is biocompatible, has good adhesion to stent struts made from stainless steel 316L, and is formed by a stable film. In other embodiments, the film is blood "permeable" rather than being a solid film. The covered sections, that is, the borders between pores or holes do not exceed 75 μm so as to prevent any part of the stent 202 or the membrane 203 from blocking perforators. Several options can be undertaken to achieve this. The membrane 203 is made from a thin film that does not exceed 0.001" in width. The film has good expandability, and can expand up to 400% at a low force. The membrane 203 also has a shelf life or chemical stability at ambient conditions and is stable in sterilization conditions (Eto).

In one example, polyurethane is used to make the membrane 203. Specifically, solution grade aromatic, polycarbonate based polyurethane is used. The physical properties are: durometer (Shore) is 75A, tensile strength is 7500 psi and elongation to 500%.

Figure 10:
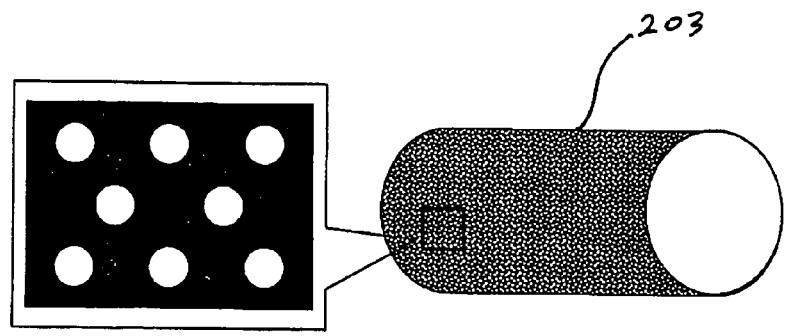
FIG. 10 is a diagrammatic view of a stent with a membrane having a pattern of pores.

Referring to FIG. 10, to make a permeable membrane 203, holes are drilled into a solid film to form pores. The pore size is between 0.025 to 0.050 mm, while the distance between pores is less than 100 μm.

Figure 11:
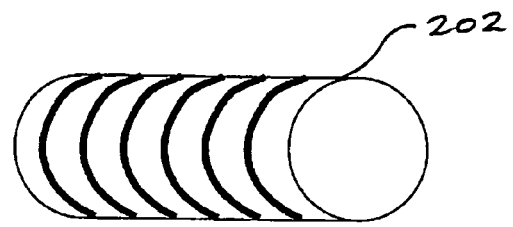
FIG. 11 is a diagrammatic view of a stent with a membrane having polymer strips.

Referring to FIG. 11, threading strips 203 of a polymer are wrapped laterally around the stent 202. The strips are interlaced above and below the struts of the stent. The width of the strips is less than 0.075 mm and distance between adjacent strips is less than 100 μm.

Figure 12:
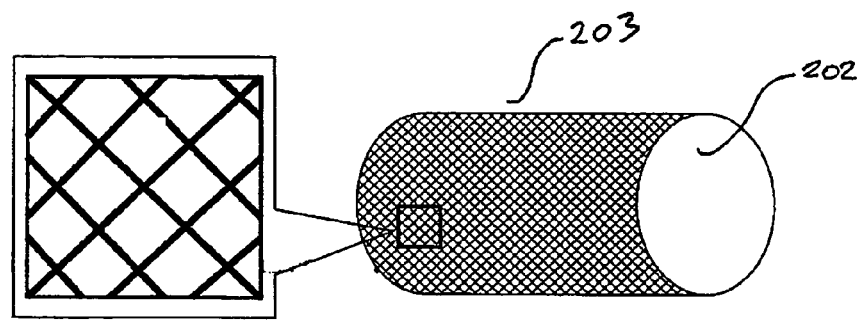
FIG. 12 is a diagrammatic view of a stent with a membrane having a mesh.

Referring to FIG. 12, a sheet of weaved material 203 is wrapped around the stent 202. The mesh size of the sheet is around 0.025-0.050 mm, while the width of the polymer is less than 100 μm.

Figure 13:
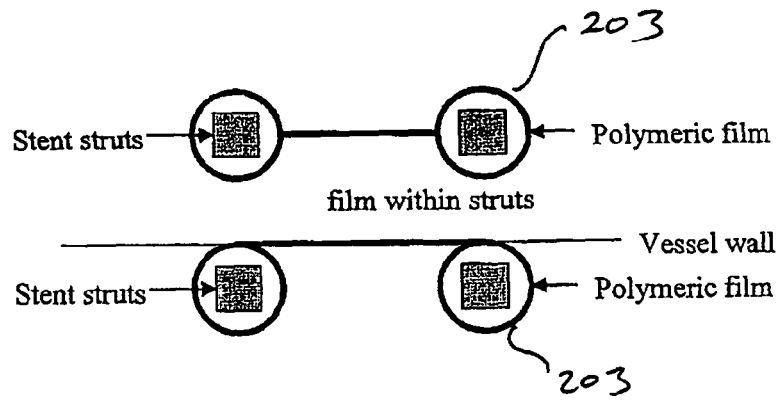
FIG. 13 is a diagrammatic view of a membrane secured to the struts of a stent.
Figure 16:
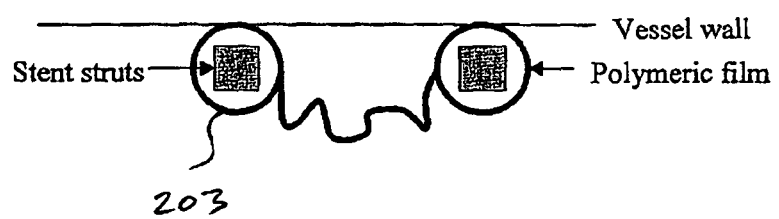
FIG. 16 is a diagrammatic view of a membrane flipping inside the vessel rather than staying close the vessel wall.

Referring to FIG. 13, the film 203 completely surrounds the stent strut and is a stable film between the struts of the stent. The film between struts is either within the struts or on the outer struts. The polymeric film stays as close to vessel wall as possible. This is to minimize the film "flipping" inside of vessel as shown in FIG. 16.

Figure 14:
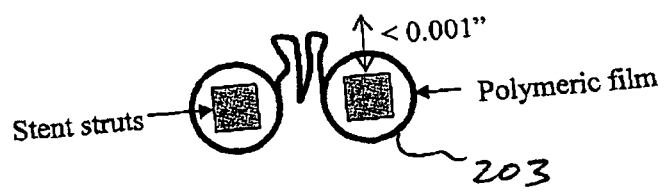
FIG. 14 is a diagrammatic view of a membrane before the stent is deployed.

Referring to FIG. 14, the membrane 203 is secured onto the struts, and is difficult to dislodge or be torn from the stent 202. The thickness of the membrane 203 does not add any significant profile to the crimped assembly, that is, it contributes to less than 0.001" of the crimped stent profile. The membrane 203 also has uniform shrinkability.

Figure 15:
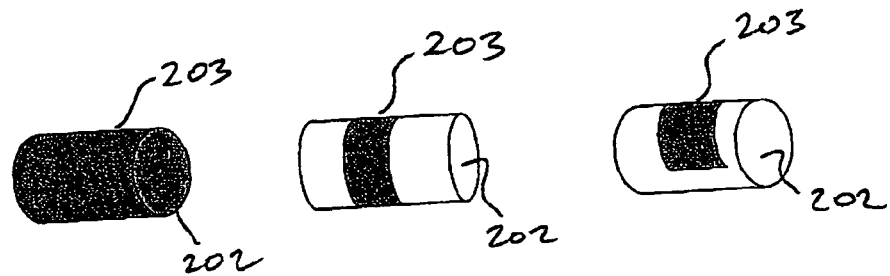
FIG. 15 is a diagrammatic view of a stent with a membrane secured at three different positions and with three different sizes.

Referring to FIG. 15, the membrane 203 may completely cover the stent 202, cover the mid-section of the stent 202, or cover a radial section of the stent 202. The membrane 203 expands with the stent 202 and does not restrict or alter the expansion characteristics of the stent 202. The membrane 203 is easily expandable up to 400%. The membrane 203 has a minimum effect on the mechanical properties of the stent 202 such as flexibility, trackability, expandability, recoil and shortening. The membrane 203 is also stable in normal shelf life conditions and stable in sterilization conditions (Eto). The properties of the polymer film are preserved and not changed after sterilization. The membrane 203 is prevented from sticking to the balloon material (Nylon) after crimping. The membrane 203 is able to tolerate temperature variations (of up to 60C). The edges of the membrane 203 are aesthetically acceptable, and have smooth, not rough edges.

Figure 17:
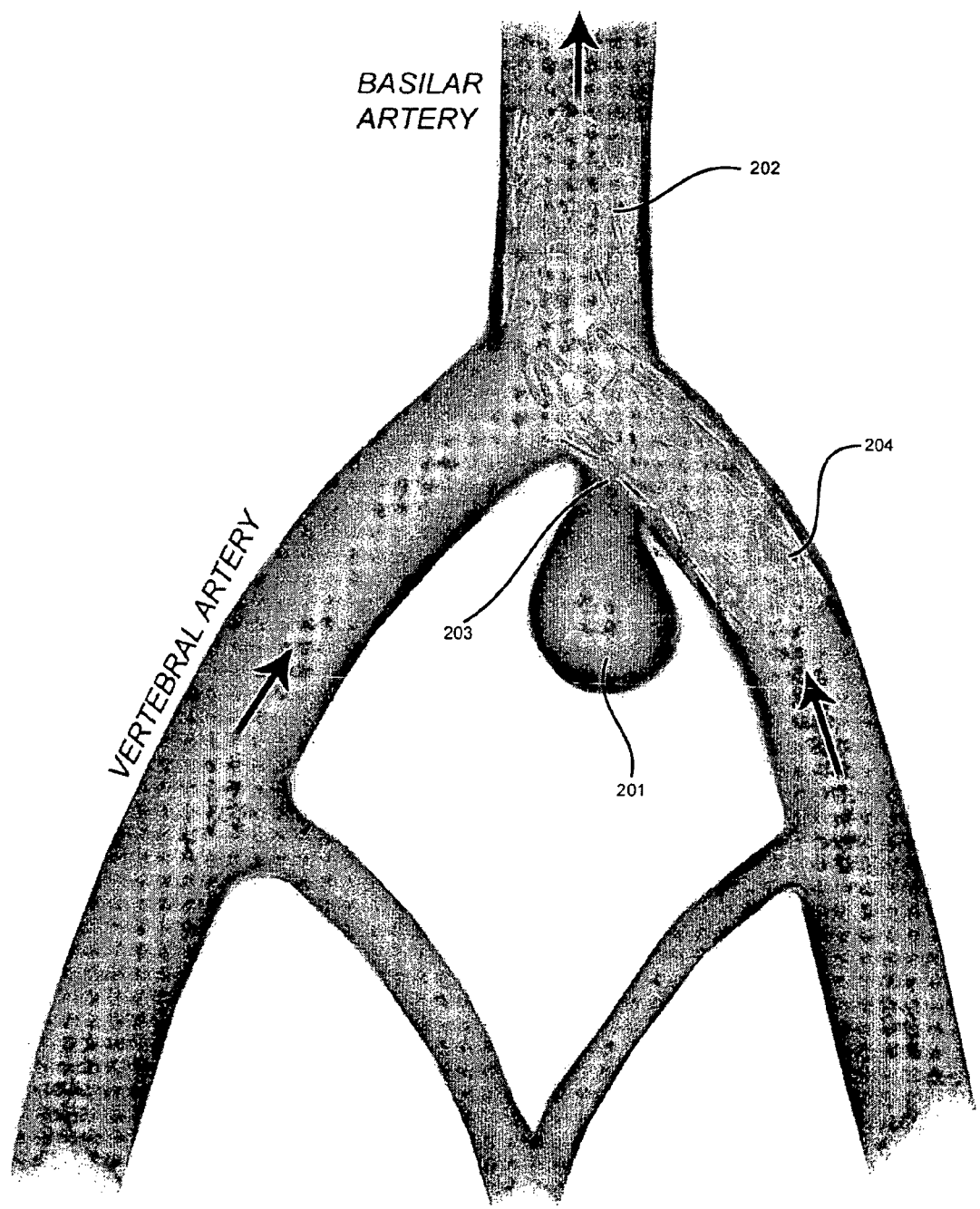
FIG. 17 is a diagrammatic view of a stent with a membrane being used to treat a bifurcation aneurysm in a first example.
Figure 18:
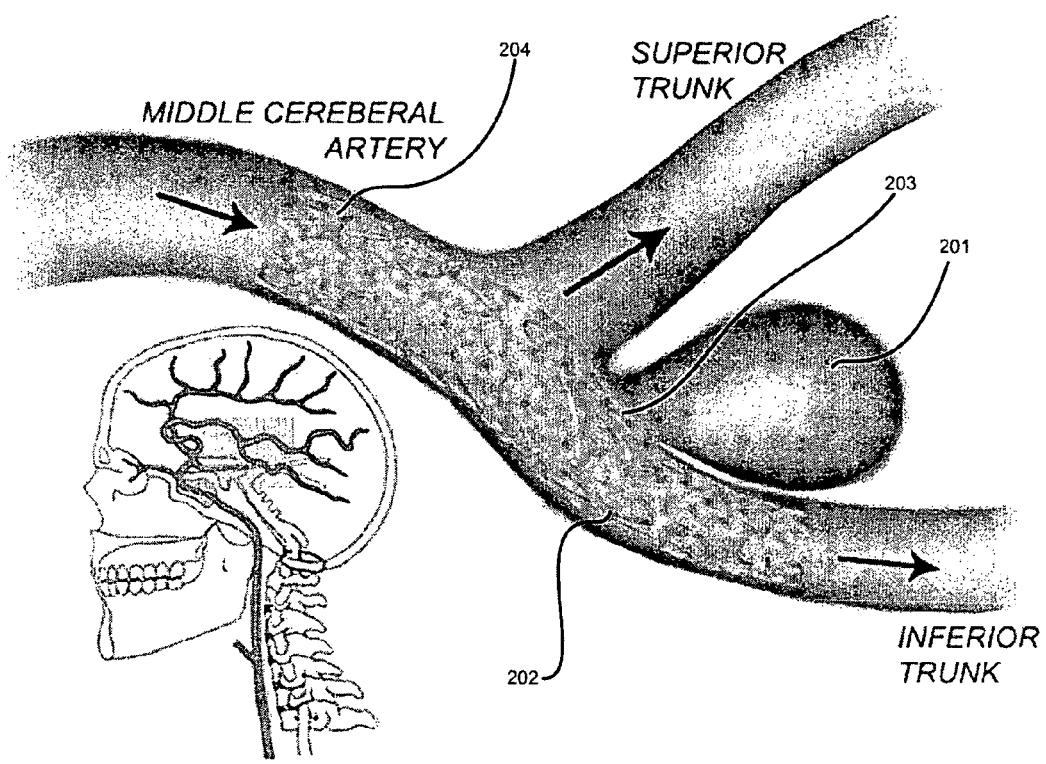
FIG. 18 is a diagrammatic view of a stent with a membrane being used to treat a bifurcation aneurysm in a second example.
Figure 19:
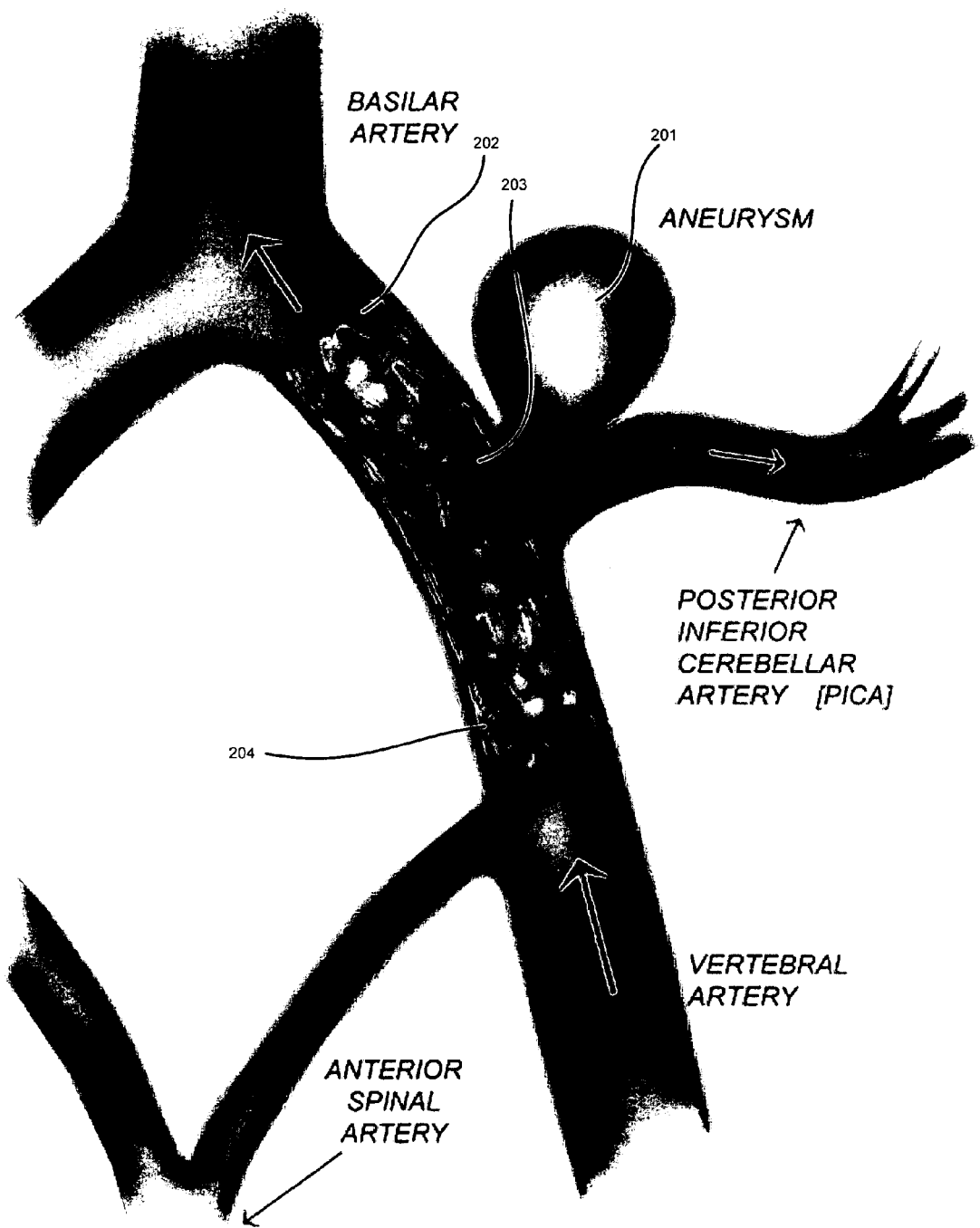
FIG. 19 is a diagrammatic view of a stent with a membrane being used to treat a bifurcation aneurysm in a third example.

Referring to FIGS. 17 to 19, the stent 202 is used to treat a bifurcation or trifurcation aneurysm 201. The stent 202 is implanted to be partially located in a main artery extending to be partially located in a subordinate artery. For example, in FIG. 17, two vertebral arteries join to the basilar artery. The stent 202 is deployed such that it is located in the basilar artery and in a vertebral artery (right side) where the aneurysm 201 is formed. On the other vertebral artery (left side), blood continues to flow to the basilar artery without any obstruction since the membrane 203 is permeable to blood flow. Preferably, the membrane 203 covers the whole stent 202, and the permeability of the membrane 203 allows blood flow through the left vertebral artery (left side).

In FIG. 18, the middle cerebral artery divides into the superior trunk and the inferior trunk. The stent 202 is deployed such that it is located in the middle cerebral artery and in the inferior trunk. Again, the struts of the stent 202 do not inhibit blood flow to the superior trunk, and blood flows through the stent 202 to the inferior trunk.

In FIG. 19, the stent 202 is deployed in the vertebral artery. As the aneurysm 201 in this example is located in a middle portion of the vertebral artery, there is no need for the stent 202 to be located in more than one artery.

When implanted, the stent 202 diverts blood flow away from the aneurysm 201. This leads to occlusion of the aneurysm 201 and keeps the arterial branches and the perforators patent. The stent 202 does not require precise positioning because preferably, it is uniformly covered with the permeable membrane 203. In other words, most of the circumferential surface of the stent 202 is covered by the membrane 203. Due to the particular porosity and dimensions of the membrane 203, blood circulation to the aneurysm 201 is obstructed while blood supply to perforators and microscopic branches of main brain arteries as well as larger arteries is permitted. As described earlier, obstructing blood supply to the aneurysm 201 isolates the aneurysm 201 from normal blood circulation, and thereby eventually causes it to dry out. The stent 202 and membrane 203 treats the aneurysm 201 by causing an alteration in the hemodynamics in the aneurysm sac such that intra-aneurysmal thrombosis is initiated. At the same, blood flow into the arteries (branch, main, big or small) are not significantly affected by the implantation of the stent 202 or the membrane 203 due to the special porosity of the membrane 203.

Although a bifurcation aneurysm has been described, it is envisaged that the stent 202 may be used to treat a trifurcation aneurysm in a similar manner.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

What is claimed:

1. A method for treating a bifurcation or trifurcation aneurysm, in a patient, occurring at a first artery, the first artery and a second artery joining to a third artery, the method comprising:

inserting a medical device partially in the first artery and partially in the third artery, the medical device comprising an expandable latticework frame having a plurality of struts that each define a radially outermost edge, a radially innermost edge, and an axial strut width, the radially outermost edge and the radially innermost edge defining a wall thickness therebetween, the medical device further comprising a porous membrane that extends around and between the plurality of struts, the membrane having a single sheet web portion that extends only in a central region, from a first strut of the plurality of struts to a second strut adjacent to the first strut, the first strut being spaced from the second strut at an interstitial spacing that is greater than the first or second axial strut width, the central region being (i) bounded radially between the radially outermost edges and the radially innermost edges of the first and second struts and (ii) bounded axially between the first strut and the second strut, the membrane web portion defining a web thickness that is less than the first or second strut wall thickness, the device having a flexibility such that the frame can be deflected 1 mm from a neutral line by applying a force against the frame of less than 8 grams;

expanding the device radially outwardly from a first position to a second position such that, when the device is in the second position, a first region of an exterior surface of the device engages an inner surface of the first artery and a second region of the exterior surface of the device engages an inner surface of the third artery, so as to maintain a fluid pathway through said arteries; and positioning the device such that, when the device is in the second position, the porous membrane, secured to the device, is located at a neck of the aneurysm;

wherein the membrane has a substantially uniform porosity over a length extending from a distal end of the membrane to a proximal end of the membrane, and a distance between adjacent pores of the membrane does not exceed 75 microns; and wherein, when the device is in the second position and the membrane is positioned at the neck of the aneurysm, the membrane is effective to:

(i) reduce blood supply into the aneurysm, and
(ii) permit blood supply through pores of the membrane and into perforators and/or microscopic branches of the first artery so as not to inhibit blood supply functions of the perforators and/or microscopic branches.

2. The method according to claim 1, wherein the device is positioned such that blood circulation to the second artery is not substantially reduced by the membrane.

3. The method according to claim 1, wherein the distance between adjacent pores of the membrane is greater than about 40 microns.

4. The method according to claim 1, wherein the membrane is made of a biocompatible and elastomeric polymer.

5. The method according to claim 1, wherein the membrane has a thickness of about 0.0005" to 0.005".

6. The method according to claim 1, wherein a ratio of a material surface area of the membrane is from about 25% to 75%.

7. The method according to claim 1, wherein the membrane has pores between 20 and 100 microns in size.

8. The method according to claim 1, wherein the membrane is made from a polymeric material or a biodegradable material.

9. The method according to claim 8, wherein the polymeric material or the biodegradable material forms multiple sublayers mixed with drugs or reagents.

10. The method according to claim 9, wherein the at least one reagent is in a form selected from the group consisting of a solid tablet, a liquid, and a powder.

11. The method according to claim 1, wherein the membrane is capable of isotropic expansion.

12. The method according to claim 1, wherein the membrane completely surrounds the plurality of struts.

13. The method according to claim 1, wherein the membrane circumferentially surrounds a portion of the device.

14. The method according to claim 1, wherein the membrane covers a portion of the device.

15. The method according to claim 1, wherein the membrane has fabricated pores between 20 and 100 microns in size.

16. The method according to claim 14, wherein the pores are fabricated by laser drilling.

17. The method according to claim 1, wherein the membrane comprises a plurality of polymeric strips.

18. The method according to claim 17, wherein the strips are less than 0.075 mm and a distance between adjacent strips is less than 100 μm.

19. The method according to claim 1, wherein the membrane comprises a mesh.

20. The method according to claim 19, wherein spaces of the mesh are less than 100 μm and a width of the meshing is between about 0.025 to 0.050 mm.

21. The method according to claim 1, wherein the aneurysm, or related clinical problem in the patient, is selected from the group consisting of a regular size aneurysm, a giant aneurysm, a wide neck aneurysm, a berry aneurysm, a CC fistula, and a fusiform aneurysm.

22. The method according to claim 1, wherein the device comprises a generally tubular structure, and wherein the exterior surface of the device is defined by a plurality of interconnected struts having interstitial spaces therebetween.

23. The method according to claim 22, wherein the membrane is supported by the generally tubular structure and is attached to at least one strut.

24. The method according to claim 1, wherein the device is self-expandable or balloon expandable.

25. The method according to claim 1, wherein the device is a stent.

26. The method according to claim 25, wherein the membrane is tubular, and wherein the membrane comprises a diameter similar to a nominal initial diameter of the stent, and wherein the membrane is disposed onto the outer surface of the stent or introduced between the struts of the stent by dip coating or by spraying.

27. The method according to claim 25, wherein the membrane is a segment of a tubular structure disposed onto a portion of the outer surface of the stent.

28. The method according to claim 1, wherein the membrane substantially covers a circumferential surface of the device.

29. The method according to claim 1, wherein the reduced blood supply into the aneurysm is effective to initiate intra-aneurysmal thrombosis.

30. The method of claim 1, wherein the wall thickness is less than or equal to 0.0028".

31. A method for treating an aneurysm, in a patient, the method comprising:
inserting a medical device partially in a first vessel and partially in a second vessel, the medical device having:
a membrane with a substantially uniform porosity over a length of the device extending from a distal end of the device to a proximal end of the device, and the membrane having a distance between adjacent pores of the membrane that does not exceed 75 microns, and
an expandable latticework frame having a plurality of struts that each define an axial strut width, a radially outermost edge, a radially innermost edge, and a wall thickness defined radially between the radially outermost edge and the radially innermost edge, the frame having a flexibility such that the frame can be deflected 1 mm from a neutral line by applying a force against the frame of less than 8 grams,
wherein the membrane extends around and between the plurality of struts, the membrane having a single sheet web portion that extends only in a central region, from a first strut of the plurality of struts to a second strut adjacent to the first strut, the first strut being spaced from the second strut at an interstitial spacing that is greater than the first or second strut width, the central region being (i) bounded radially between the radially outermost edges and the radially innermost edges of the first and second struts and (ii) bounded axially between the first strut and the second strut, the membrane web portion defining a web thickness that is less than the first or second strut wall thickness;
expanding the device radially outwardly from a first position to a second position such that, when the device is in the second position, a first region of an exterior surface of the device engages an inner surface of the first vessel and a second region of the exterior surface of the device engages an inner surface of the second vessel, so as to maintain a fluid pathway through each vessel; and
positioning the device such that, when the device is in the second position, the membrane is located at a neck of the aneurysm such that the membrane:
(i) reduces blood flow into the aneurysm, and
(ii) permits blood supply to perforator vessels through pores of the membrane along the length of the membrane so as not to inhibit blood supply functions of the perforator vessels.

32. The method according to claim 31, wherein the device is positioned such that blood circulation to the perforator vessels is not substantially reduced by the membrane.

33. The method according to claim 31, wherein the distance between adjacent pores of the membrane is greater than about 40 microns.

34. The method according to claim 31, wherein the membrane is made of a biocompatible and elastomeric polymer.

35. The method according to claim 31, wherein the membrane has a thickness of about 0.0005" to 0.005".

36. The method according to claim 31, wherein a ratio of a material surface area of the membrane is from about 25% to 75%.

37. The method according to claim 31, wherein the membrane has pores between 20 and 100 microns in size.

38. The method according to claim 31, wherein the membrane completely surrounds each of the plurality of struts.

39. The method according to claim 31, wherein the membrane comprises a mesh.

40. The method according to claim 39, wherein spaces of the mesh are less than 100 μm and a width of the meshing is between about 0.025 to 0.050 mm.

41. The method according to claim 31, wherein the device comprises a generally tubular structure, and wherein the exterior surface of the device is defined by a plurality of interconnected struts having interstitial spaces therebetween.

42. The method according to claim 31, wherein the membrane substantially covers a circumferential surface of the device.

43. The method according to claim 31, wherein the reduced blood supply into the aneurysm is effective to initiate intra-aneurysmal thrombosis.

44. The method of claim 31, wherein the membrane comprises a durometer of 75A Shore, a tensile strength of 7500 psi, and can be elongated to 500%.

45. The method of claim 31, wherein the wall thickness is less than or equal to 0.0028".

46. A method for treating an aneurysm, in a patient, the method comprising:
inserting a medical device in a first vessel, the medical device having attached therewith a porous membrane with a substantially uniform porosity, and an expandable latticework frame having a plurality of struts that each define an axial strut width, a radially outermost edge, a radially innermost edge, and a wall thickness defined between the radially outermost edge and the radially innermost edge, the device having a flexibility such that the frame can be deflected 1 mm from a neutral line by applying a force against the frame of less than 8 grams, wherein the porous membrane extends around and between the plurality of struts, the membrane having a single sheet web portion that extends only in a central region, from a first strut of the plurality of struts to a second strut adjacent to the first strut, the first strut being spaced from the second strut at an interstitial spacing that is greater than the first or second strut width, the central region being (i) bounded radially between the radially outermost edges and the radially innermost edges of the first and second struts and (ii) bounded axially between the first strut and the second strut, the membrane web portion defining a web thickness that is less than the first or second strut wall thickness;
positioning the device such that the device and membrane is located at a neck of the aneurysm; and
expanding the device radially outwardly from a first position to a second position such that, when the device is in the second position, a distal region of an exterior surface of the device engages an inner surface of the first vessel distal to the aneurysm, a proximal region of the exterior surface of the device engages an inner surface of the first vessel proximal to the aneurysm;
wherein, when the device is in the second position, the membrane comprises pores with a size between about 20 microns and about 100 microns and a distance between adjacent pores that is not larger than 100 microns, such that the membrane reduces blood flow into the aneurysm and permits blood supply to small branch vessels, branching from the first vessel, through the pores of the membrane so as not to inhibit blood supply functions of the small branch vessels.

47. The method according to claim 46, wherein the distance between adjacent pores does not exceed 75 microns.

48. The method according to claim 46, wherein the distance between adjacent pores is from about 40 microns to 100 microns.

49. The method according to claim 46, wherein the device is positioned such that blood circulation to the perforator vessels is not substantially reduced by the membrane.

50. The method according to claim 46, wherein the membrane is made of a biocompatible and elastomeric polymer.

51. The method according to claim 46, wherein the membrane has a thickness of about 0.0005" to 0.005".

52. The method according to claim 46, wherein a ratio of a material surface area of the membrane is from about 25% to 75%.

53. The method according to claim 46, wherein the membrane completely surrounds the plurality of struts.

54. The method according to claim 46, wherein the membrane comprises a mesh.

55. The method according to claim 54, wherein spaces of the mesh are less than 100 μm and a width of the meshing is between about 0.025 to 0.050 mm.

56. The method according to claim 46, wherein the device comprises a generally tubular structure, and wherein the exterior surface of the device is defined by a plurality of interconnected struts having interstitial spaces therebetween.

57. The method according to claim 46, wherein the membrane substantially covers a circumferential surface of the device.

58. The method according to claim 46, wherein the reduced blood supply into the aneurysm is effective to initiate intra-aneurysmal thrombosis.

59. The method of claim 46, wherein the membrane comprises a durometer of 75A Shore, a tensile strength of 7500 psi, and can be elongated to 500%.

60. The method of claim 46, wherein the wall thickness is less than or equal to 0.0028".

* * * * *